US006238646B1

(12) United States Patent
Zembrodt

(10) Patent No.: US 6,238,646 B1
(45) Date of Patent: May 29, 2001

(54) AQUEOUS AEROSOL COMPOSITIONS FOR DELIVERY OF ATOMIZED OIL

(75) Inventor: Anthony R. Zembrodt, Covington, KY (US)

(73) Assignee: Global Technology Transfer, L.L.C., Park Hills, KY (US)

( * ) Notice: Subject to any disclaimer, the term of this patent is extended or adjusted under 35 U.S.C. 154(b) by 0 days.

(21) Appl. No.: 09/322,435

(22) Filed: May 28, 1999

(51) Int. Cl.$^7$ ......................................................... A61K 9/12
(52) U.S. Cl. ........................... 424/45; 424/76.1; 424/401; 424/DIG. 10; 514/63; 514/938
(58) Field of Search .............................. 424/DIG. 10, 45, 424/76.1, 401; 514/938, 63

(56) References Cited

U.S. PATENT DOCUMENTS

| | | | |
|---|---|---|---|
| 3,207,386 | 9/1965 | Presant et al. | 222/394 |
| 3,948,817 | 4/1976 | Grothoff | 252/522 |
| 4,110,428 | 8/1978 | Kuhn et al. | 424/46 |
| 4,254,104 | 3/1981 | Suzuki | 424/170 |
| 4,382,078 | 5/1983 | Berkhoff | 424/45 |
| 4,444,745 | 4/1984 | Jacobson et al. | 424/45 |
| 4,518,734 | 5/1985 | Brouillette et al. | 525/378 |
| 4,536,323 | 8/1985 | Stopper | 252/305 |
| 4,585,577 | 4/1986 | Bartlett et al. | 252/305 |
| 4,595,522 | 6/1986 | Bartlett et al. | 252/305 |
| 4,655,959 | 4/1987 | Stopper | 252/305 |
| 4,938,416 | 7/1990 | Bertrand et al. | 239/1 |
| 5,620,678 | 4/1997 | Burke | 424/45 |
| 5,830,440 | 11/1998 | Sturla et al. | 424/47 |

OTHER PUBLICATIONS

BF Goodrich, Polymers for Personal Care: Formulation Guide, Sep. 1997.
BF Goodrich Home Care and I & I, Solutions Close to Home: Formulary Guide, May, 1998.

*Primary Examiner*—Raj Bawa
(74) *Attorney, Agent, or Firm*—Wood, Herron & Evans, L.L.P.

(57) ABSTRACT

Aqueous aerosol compositions are produced particularly for the delivery of an atomized oil, such as a fragrance oil, insecticidal oil or medicinal oil. The water based system, which includes a water soluble propellant and a dispersed oil phase in water with a polymeric emulsion, does not need shaking before use, is not flammable, and leaves no deposition on surfaces.

12 Claims, No Drawings

AQUEOUS AEROSOL COMPOSITIONS FOR DELIVERY OF ATOMIZED OIL

TECHNICAL FIELD OF THE INVENTION

This invention is directed to aqueous aerosol compositions, particularly for the delivery of an atomized oil such as a fragrance oil, insecticidal oil and medicinal oil.

BACKGROUND OF THE INVENTION

In the past, different aerosol formulations have been used to deliver atomized oil particles. One type of aerosol composition contained an oil, co-solvent and propellant typically for dispensing a small amount of an oil, such as a perfume. A second type of aerosol used simply an oil and propellant. These aerosols were called dry systems because the components vaporized upon spraying. A third type of aerosol is an aqueous based system which complies with EPA Regulations for Volatile Organic Compounds (VOC) primarily because they have water as the major component. One of the major problems with an aqueous aerosol has been the need to shake the system before use, just as when one mixes oil and vinegar they separate, the same thing occurs with this system. Typically, a "shake before using" statement is on the label of these products to avoid spraying only one phase through the dip tube of the spray can while the other phase remains in the can. In many cases, it is not practical or possible to shake the container before use and, thus, these systems have limitations. Where room air fresheners are formulated employing the three types of aerosols, usually about 25–50% of a perfume is contained in the first type, about 2–10% perfume is contained in the second type, and the third type usually contains about 1% perfume.

Two main types of water-based aerosols have been known, namely, a three-phase system and a two-phase system. The three-phase aerosol system is formed when using a propellant such as propane or butane which is insoluble in the water phase. These three-phase aerosol systems need to be shaken properly before use. Two-phase aqueous aerosol systems consist of a homogeneous liquid phase and a gaseous phase. The liquid phase usually contains the active ingredients, solvents and liquified propellant. Homogeneity is achieved by means of a water soluble propellant such as dimethyl ether (DME). These types of aerosols need not be shaken before use. However, it has been difficult to obtain homogeneous DME-water mixtures which are stable upon standing. Attempts have been made to solve the stability problem by developing special perfumes or by the addition of special solvents. U.S. Pat. No. 4,382,078 is an example of a prior approach to solve the stability problem by employing a copolymer of ethylene oxide and propylene oxide as a surfactant to retain the active ingredients in the liquid phase.

Furthermore, in this '078 patent, with increasing amounts of fragrance oil, increasing amounts of surfactant are required. Increased surfactant results in non-volatile material being sprayed which is undesirable because of unwanted deposition on surfaces, among other environmental deficiencies.

There exists a need for an aqueous aerosol composition for the delivery of atomized oil such as a fragrance oil, insecticidal oil and medicinal oil without the disadvantages associated with presently available systems.

SUMMARY OF THE INVENTION

This invention is directed to an aqueous aerosol composition containing water, water soluble propellant, dispersed oil phase in the water, nonionic surfactant and a polymeric emulsifier. The components of the composition are contained in relative amounts to provide a viscosity for delivery of atomized particles of the oil.

In accordance with the principles of this invention, a water based system is used to give a concentrated aqueous system that does not need shaking, is not flammable, and performs like a concentrated non-aqueous system. This invention is predicated in part upon the use of a polymeric emulsifier that forms a matrix into which the oil can be trapped. A nonionic surfactant helps suspend the oil particles by decreasing the droplet size of the dispersed phase in the water. A water soluble propellant, such as dimethyl ether has been found to provide the composition with satisfactory delivery of atomized oil particles. The aqueous aerosol compositions of this invention have been found to provide substantial stability on standing for many months. Furthermore, atomized particles are delivered by the compositions without bearding and with a consistent spray pattern during the life of the product. In contrast to other water-based aerosol systems, the compositions of this invention do not require shaking before use, notwithstanding the unique three-phase system of the polymer matrix, oil and water. Heretofore, three-phase aerosol systems have required shaking before use. In this regard, this is considered one of the unexpected advantages of the composition of this invention.

Another advantage of the aqueous aerosol compositions of this invention is the ability to use varying amounts of oil from about 0.1% to about 30% by weight while even employing one low level of polymeric emulsifier. It has been found that a minor amount of polymeric emulsifier, on the order of about 0.05% to about 0.4% by weight, is capable of physically suspending or emulsifying significant amounts of perfume in a three dimensional matrix and holds them there in what might be considered a thermodynamically unstable form. The oil particles are surrounded by the surfactant which helps hold them in suspension. In this regard, very minor amounts of surfactant, on the order of only about 0.1% to about 1% by weight, are necessary to hold the oil particles in solution.

A water soluble propellant such as dimethyl ether and methylethyl ether is required in order to obtain the benefits of this invention. In particular, the aqueous solutions do not exhibit flame extensions, and aerosol containers using the system comply with VOC regulations (EPA regulations for Volatile Organic Compounds, Section 183(e), Clean Air Act, 40 CFR, Chapter 1, pages 48,792—48,887). Furthermore, the inventive aqueous aerosol compositions perform at least at parity to the non-aqueous aerosol systems. An amount of a hydrocarbon propellant selected from the group consisting of propane, isobutane, butane, and mixtures thereof, may be employed with the water soluble propellant. When so employed, the hydrocarbon propellant is usually contained in an amount of from about 50% to about 20% by weight of the water soluble propellant, such as dimethyl ether.

Other advantages and objectives of this invention will be further understood with reference to the following detailed description.

DETAILED DESCRIPTION

A preferred aqueous aerosol composition of this invention and a range of components that may be satisfactorily employed is illustrated by the following table.

| Component | Preferred Amount (% by weight) | Range (% by weight) |
|---|---|---|
| Propellant Dimethyl ether (DME) | 28 | about 20 to about 40 |
| Perfume | 4 | about 0.5 to about 30 |
| Polymeric emulsifier Pemulen 1622 | 0.18 | 0.0.05–0.40 |
| Disodium EDTA | 0.036 | 0.01–0.06 |
| Pluronic 10R5 surfactant | 0.36 | 0.1–1.0 |
| Triethanolamine (TEA) | 0.27 | 0.05–0.45 |
| Viscosity modifier Goodrite 752 | 0.36 | 0.05–0.45 |
| Water | 66.8 | balance |

Pemulen 1622 is a polymeric emulsifier made by B. F. Goodrich and is described as a copolymer of acrylic acid and $C_{10-30}$ alkyl acrylate cross-linked with polyalkenyl ether. More generically suitable polymeric emulsifiers according to this invention are selected from the group consisting of polyacrylic acid homopolymer and copolymers thereof such as Pemulen 1622 which is a copolymer of a polyalkyl acrylate. The disodium ethylene diaminetetraacetic acid (EDTA) is employed to complex metal ions which may otherwise destabilize the emulsion. Pluronic 10R5 is a block copolymer of ethylene oxide and propylene oxide which is employed as a surfactant. Other surfactants that are suitable include nonylphenol polyoxyethylene, ethyoxylated alcohol and polyoxyethylene sorbitan monooleate. Triethanolamine is employed to adjust and stabilize the pH of a composition. Goodrite 752 is a viscosity modifier, also made by B. F. Goodrich, and is described as a water soluble polyacrylic acid or polymethylacrylic acid, and copolymers thereof, typically copolymerized with a sulfonic acid and a styrene sulfonate. The above components are thus provided in relative amounts to provide viscosity adjustments for the delivery of atomized particles of the oil. Satisfactory viscosities for room air freshening, for example, are on the order of about 200–400 cp at 25° C., Brookfield RVT @ 20 rpm, #2 spindle.

One method of making the presently preferred aqueous aerosol for use as an air freshener employing the specific components of Table 1 involves first stirring the Pemulen 1622 in water to completely hydrate the polymeric emulsifier to form a stable dispersion. Minor amounts of Pemulen, from about 0.5% up to about 0.4% by weight, are employed to achieve a stable dispersion without producing a product which becomes like molasses and is difficult to spray. Fragrance oil is then added, preferably avoiding air, in order to capture the oil in the polymeric emulsifier matrix to form a macro emulsion with the fragrance oil contained in the form of a physical emulsion in the matrix. The Pluronic 10R5 is then added to coat the fragrance oil particles and decrease the particle size to provide a storage stable product. The disodium EDTA is added to capture ions which would tend to destabilize the emulsion, and triethanolamine is added to neutralize the carboxylic acid groups on the polymer matrix of the emulsifier. At this point in the processing, a milky liquid having a viscosity of about 800–1500 cP is obtained (Brookfield RVT @20 rpm, #2 spindle). In order to reduce the viscosity to an acceptable level for practical room spraying, the Goodrite K752 is added to decrease the apparent viscosity to about 200–400 cP. The final composition is then placed in a can and the DME is forced into the can to achieve an equilibrium pressure inside the can of about 67 psig at 70° F. Room spray is delivered from the can at about 0.49 gms/sec, which is consumer acceptable.

Any perfumes may be employed as air fresheners to provide such odors as woody, fruity, spicy, earthy, and the like. As mentioned above, the oils may be any one of a member of a class of oils described as insecticides, silicones, medicinal agents, and the like. In view of the above detailed description and operating examples, a person of ordinary skill in the art will understand that other modifications and embodiments may be derived without departing from the spirit and scope of this invention.

What is claimed is:

1. An aqueous aerosol air freshener for room spraying composition for the delivery of atomized particles of oil comprising water, a water soluble propellant selected from the group consisting of dimethyl ether and methylethyl ether, about 0 to about 30 percent by weight of a dispersed oil phase in the water, a nonionic surfactant and about 0.05 to about 0.4 percent by weight of a polymeric emulsifier selected from the group consisting of polyacrylic homopolymer and copolymers thereof, said components in relative amounts to provide a viscosity for delivery of atomized particles of the oil.

2. The composition of claim 1 wherein the copolymer is a polyalkylacrylate.

3. The composition of claim 1 wherein the nonionic surfactant is selected from the group consisting of a block copolymer of ethylene oxide and propylene oxide, nonylphenol polyoxyethylene, ethyoxylated alcohol, and polyoxyethylene sorbitan monooleate.

4. The composition of claim 1 further containing a water soluble polymer as a viscosity modifier.

5. The composition of claim 4 wherein the water soluble polymer is selected from the group consisting of a water soluble polyacrylic acid, polymethylacrylic acid, and copolymers thereof.

6. The composition of claim 1 further comprising a hydrocarbon propellant selected from the group consisting of propane, isobutene, butane, and mixtures thereof in an amount of from about 50 to about 20 percent by weight of said water soluble propellant.

7. An aqueous aerosol air freshener for room spraying composition for delivery of atomized particles of a fragrance oil consisting essentially of about 20% to about 40% by weight dimethyl ether propellant, about 0.5% to about 30% by weight fragrance oil, about 0.05% to about 0.4% by weight of a polymeric emulsifier selected from the group consisting of polyacrylic homopolymer and copolymers thereof, a nonionic surfactant, a pH modifier, a viscosity modifier, and the balance water.

8. The composition of claim 7 wherein the surfactant is a block copolymer of ethylene oxide and propylene oxide in an amount of from about 0.1% to about 1% by weight, and the viscosity modifier is a water soluble polyacrylate polymer in an amount of from about 0.05% to about 0.45% by weight.

9. The composition of claim 8 further containing a chelating agent and a pH modifier.

10. The composition of claim 8 further containing a hydrocarbon propellant selected from the group consisting of propane, isobutant, butane, and mixtures thereof, in an amount of from about 50% to about 20% by weight of said dimethyl ether.

11. An aqueous aerosol air freshener for room spraying composition for delivery of atomized particles of oil consisting essentially of about 20% to about 30%, by weight dimethyl ether propellant, about 0.5% to about 30% by weight oil, about 0.05% to about 0.4% by weight of a polymeric emulsifier selected from the group consisting of polyacrylic homopolymer and copolymers thereof, about 0.05% to about 0.45% by weight of water soluble polyacrylate polymer as a viscosity modifier, about 0.1% to about 1% by weight of a block polymer of ethylene oxide and propylene oxide, about 0.01% to about 0.06% by weight of disodium EDTA, about 0.05% to about 0.45% by weight of triethanolamine pH modifier, and the balance water.

12. The composition of claim 11 wherein the oil is selected from the group consisting of a fragrance oil, insecticidal oil, medicinal oil, and silicone oil.

* * * * *

UNITED STATES PATENT AND TRADEMARK OFFICE
CERTIFICATE OF CORRECTION

PATENT NO.     : 6,238,646 B1
DATED          : May 29, 2001
INVENTOR(S)    : Anthony R. Zembrodt It is certified that error appears in the above-identified patent and that said Letters Patent is hereby corrected as shown below:

<u>Column 4, claim 1,</u>
Line 14, "about 0 to about 30 percent by weight" should be -- about 0.1 to about 30 percent by weight --

<u>Column 4, claim 6,</u>
Line 35, "isobutene" should be -- isobutane --

Signed and Sealed this

Nineteenth Day of March, 2002

Attest:

Attesting Officer

JAMES E. ROGAN
Director of the United States Patent and Trademark Office